United States Patent
Woo et al.

(10) Patent No.: US 7,268,238 B2
(45) Date of Patent: Sep. 11, 2007

(54) MANUFACTURING METHOD AND APPARATUS OF 4-FLUOROETHYLENE CARBONATE

(75) Inventors: Byung Won Woo, Ulsan (KR); Seoung Woo Yoon, Ulsan (KR); Jun Ho Lee, Ulsan (KR); Soon Hong Park, Ulsan (KR); Nak Joon Jang, Ulsan (KR); Hyo Jin Yoon, Ulsan (KR)

(73) Assignee: Ulsan Chemical Co., Ltd., Ulsan (KR)

( * ) Notice: Subject to any disclaimer, the term of this patent is extended or adjusted under 35 U.S.C. 154(b) by 415 days.

(21) Appl. No.: 11/072,123

(22) Filed: Mar. 7, 2005

(65) Prior Publication Data
US 2006/0167279 A1 Jul. 27, 2006

(30) Foreign Application Priority Data
Jan. 24, 2005 (KR) .................... 10-2005-0006260

(51) Int. Cl.
*C07D 317/42* (2006.01)
(52) U.S. Cl. ...................................... 549/296
(58) Field of Classification Search ................. 549/296
See application file for complete search history.

(56) References Cited

U.S. PATENT DOCUMENTS 6,010,806 A  1/2000 Yokoyama

FOREIGN PATENT DOCUMENTS

| JP | 2000-309583 | 4/1999 |
| JP | 2000-344763 | 6/1999 |
| JP | 2004-063432 | 8/2002 |
| WO | WO 98/15024 | 4/1998 |
| WO | WO 2004/076439 | 9/2004 |

*Primary Examiner*—Taofiq Solola
(74) *Attorney, Agent, or Firm*—Egbert Law Offices

(57) ABSTRACT

The method of producing 4-fluoroethylene carbonate (FEC), in which ethylene carbonate (EC) reacts with a mixture of fluorine and nitrogen gases, includes feeding a mixture gas of fluorine gas and nitrogen gas into a reactor having ethylene carbonate charged therein, so as to react the ethylene carbonate with the mixture gas of the fluorine gas and the nitrogen gas. The mixture gas fed in the reactor is regulated to have a desired bubble size while passing through a gas bubble regulating column, in which a packing for a packed column is packed. In the method, EC directly reacts with $F_2/N_2$ mixture gas to produce FEC, thus a purification process is simple and it is possible to produce FEC at high conversion efficiency and selectivity.

5 Claims, 2 Drawing Sheets

MANUFACTURING METHOD AND APPARATUS OF 4-FLUOROETHYLENE CARBONATE

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates to a method and a device for producing 4-fluoroethylene carbonate. More particularly, the present invention pertains to a method of producing 4-fluoro-1,3-dioxolan-2-one, in which ethylene carbonate (($CH_2O)_2CO$, hereinafter referred to as "EC") directly reacts with a mixture gas of fluorine and nitrogen gases (hereinafter, referred to as "$F_2/N_2$ mixture gas") without using a solvent, and a device used in the method.

2. Description of Related Art Including Information Disclosed Under 37 CFR 1.97 and 37 CFR 1.98.

4-fluoro-1,3-dioxolan-2-one has the common name 4-fluoroethylene carbonate (hereinafter, referred to as "FEC").

An insoluble organic electrolyte, in which $F_2$-containing inorganic lithium salts are dissolved in an organic solvent, is mainly used as an electrolyte for lithium ion secondary batteries. With respect to this, the electrolyte must be highly conductive, and electrically and chemically stable, and have low reactivity to a vessel and electrode material. Typically, one organic solvent cannot have all of the above various properties, thus a mixture of the organic solvents is used. Furthermore, it is known that performance of the lithium ion secondary battery is improved by adding an $F_2$-containing organic compound to the electrolyte mixture, and fluoroethylene carbonates are frequently used as the $F_2$-containing organic compound.

Fluoroethylene carbonate is classified into mono-fluoroethylene carbonate, di-fluoroethylene carbonate, tri-fluoroethylene carbonate, tetra-fluoroethylene carbonate, and isomers thereof according to the number of substituted fluorine atoms. Of them, FEC is known as the best additive capable of improving performance of the organic solvent for the electrolyte of the lithium ion secondary battery. If FEC is added as the additive to the electrolyte, reduction of performance of the battery caused by decomposition of the electrolyte is insignificant during an initial electrification, and explosions intermittently occurring in the lithium ion secondary battery are suppressed because the thermal stability of the battery is significantly improved. Due to these functions, the use of FEC is gradually growing.

However, in order to assure performance and safety of the battery, the quality of FEC, which is capable of being used as the electrolyte of the lithium secondary battery, is very strictly regulated so that purity is 99.8 wt % or more, moisture content is 20 ppm or less, APHA color is 50 or less, metal ion content is 1 ppm or less, and acidity (based on HF) is 50 ppm or less.

With respect to the production of FEC, a method of directly reacting EC with $F_2/N_2$ mixture gas to fluorinate EC is known as the best method in view of yield and purity. If EC directly comes into contact with $F_2$ gas and they thus react with each other, reactivity is very high, causing local explosions, resulting in deterioration of EC. Accordingly, various modified methods, such as the use of the $F_2/N_2$ mixture gas and the use of fluoride, having low reactivity to $F_2$, as a reaction solvent, are adopted so as to assure stability of the reaction.

U.S. Pat. No. 6,010,806 (from the year 2000) discloses a method of producing tri-fluoroethylene carbonate, in which dimethyl carbonate reacts with 3,3,3-trifluoro-1,2-propylene oxide in the presence of sodium carbonate ($NaHCO_3$).

In the above method, costly fluoro-organics (3,3,3-trifluoro-1,2-propylene oxide) are employed as a raw material, and a reaction time is 8-40 hours, which is somewhat long. Additionally, an agitation unit is used in a cylindrical reactor, and rinsing is conducted using water to produce a final product. Furthermore, complicated purification processes, such as extraction, drying, filtration, and crystallization of organics, are conducted, and yield is no more than 57%. Since the complicated purification processes are repeated, the possibility of inflow of impurities is increased. Accordingly, it is difficult to assure a desirable quality electrolyte for the lithium ion secondary battery (in which a metal component content is 1 ppm or less, a moisture content is 20 ppm or less, and acidity is 50 ppm or less), thus the above method may not be applied to a commercial process.

WO 98/15024 discloses a method of synthesizing FEC through a fluorine substitution reaction using 4-chloro-1,3-dioxolan-2-one and KF. In this method, the halogen substitution reaction requires a high temperature and a long reaction time, selectivity is low, and a post-process, such as a rinsing process employing water or filtration, is inevitably conducted to remove used KF, and KCl and HCl byproducts. It is very difficult to produce highly pure FEC through the above complicated purification process.

Japanese Patent Laid-Open Publication No. 2000-309583 discloses a method of producing FEC, in which EC is used as a raw material in a reactor having a thermostatic bath at 50° C. and an agitator in the bath. Anhydrous hydrogen fluoride or perfluoro carbon is used as a reaction solvent, 30% $F_2/N_2$ mixture gas is fed at a flow rate of 350 ml/min, a reaction is conducted for about 40 hours while agitation is implemented at 800 rpm, and rinsing is conducted using water to remove HF. The rinsing is conducted again using 10% $NaHCO_3$ aqueous solution, and extraction is conducted six times using 500 ml of dichloromethane. After drying is conducted using $MgSO_4$, dichloromethane is removed, and distillation and crystallization processes are carried out. In the method, when 1.8 mol $F_2$ gas are used, the FEC content of reactants is 64-67%, which means that 33-35 mol % of supplied $F_2$ gas is consumed in the reaction and 3 mol $F_2$ gas are needed to produce 1 mol FEC. Since 33% of supplied $F_2$ gas is consumed in the reaction, the great amount of FEC is dissolved in water during the rinsing and extraction processes, thus the yield is rapidly reduced. Furthermore, vinylene carbonate is generated as a byproduct through dehydro fluorination of FEC due to moisture, thus purification may be impossible. As well, undesirably, anhydrous hydrofluoric acid is used in an amount of 5-50% of an EC weight ratio to control reaction heat, and costly $F_2$ gas is used in an excessive amount of 1.8 mol based on EC. In the above reaction, FEC having a purity of 90% is produced in an amount of 480 g (70% yield). Re-crystallization is repeated a few times at 15° C. to produce 390 g of FEC having a purity of 99% or more. At this time, yield is 38% based on the amount of $F_2$ used.

Japanese Patent Laid-Open Publication No. 2000-344763 discloses a method of producing highly pure difluoro ethylene carbonate, in which 30% $F_2/N_2$ mixture gas is added at a flow rate of 250 ml/min to EC in a reaction device that is the same as that of Japanese Patent Laid-Open Publication No. 2000-309583. Reaction is conducted for about 11 hours to produce difluoroethylene carbonate (hereinafter, referred to as "DFEC") which contains 70% trans, 14% cis, 6% gem, and 9% FEC. After HF is removed by distillation, rinsing is conducted using 10% $NaHCO_3$ aqueous solution, and extraction is conducted six times using 250 ml of dichloromethane. Thereafter, drying is conducted using $MgSO_4$, and DFEC is separated by vacuum distillation at 5-20 mmHg. In this reaction, the amount of $F_2$ used is 2.25 mol based on 1 mol EC, and purity is 99% or more after re-crystallization.

In Japanese Patent No. 2004-63432, 3 mol $F_2$ gas are needed to produce 1 mol FEC. This patent is problematic in that since water is used to remove HF, problems with respect to reduced yield as described above occur.

WO 2004/076439 (Application No. PCT/EP 2004/001345) discloses a method of producing FEC, in which FEC is mixed with EC in an amount of 3-20 wt % based on a weight ratio of EC and is then reacted with 5 v/v % $F_2/N_2$ mixture gas at a low temperature of about 15-45° C. so as to control the temperature of an intense reaction between EC and fluorine gas or $F_2/N_2$ mixture gas. Neutralization is conducted using $KHCO_3$ after the reaction is finished. After filtration, the filtrate is washed with acetone, and the acetone is removed by distillation. In this method, the time required to produce FEC is 4-5 times as long as that of the present invention, and distillation is conducted after a neutralization process using potassium hydrogen bicarbonate ($KHCO_3$), a suspension filtration process, and a washing process using acetone. Therefore, a production process is complicated, the possibility of inflow of impurities is high, and it is commercially nonviable.

In Japanese Patent Laid-Open Publication Nos. 2000-309583 and 2000-344763, EC is dissolved in an anhydrous hydrogen fluoride solution so that an EC content is 5-50 wt %, and a $F_2/N_2$ mixture gas is supplied and then reacted. However, these patents are disadvantageous in that since HF is generated in 20 wt % of the amount of FEC only through the reaction between EC and the $F_2/N_2$ mixture gas, it is not easy to reduce the amount of HF to a set value or less after the reaction is finished. Accordingly, it is difficult to apply these patents to a commercial process and they are economically inefficient. Furthermore, it is difficult to reduce the acidity, which is the most important property of an electrolyte, to a set value or less even when a re-crystallization process is implemented.

BRIEF SUMMARY OF THE INVENTION

Accordingly, an object of the present invention is to provide a method of producing FEC through a direct reaction between EC and $F_2/N_2$ mixture gas, which is implemented under moderate reaction conditions and in which conversion efficiency and selectivity are excellent and a highly pure product is produced through a simple purification process, and a reaction device useful to produce FEC.

In a method of producing FEC through a direct reaction between EC and $F_2/N_2$ mixture gas, the present inventors have observed that, when EC liquid came into contact with the $F_2/N_2$ mixture gas, the $F_2/N_2$ mixture gas reacted with EC while generating bubbles in EC liquid, and the reaction was rapid when the bubbles were large, causing local explosions, resulting in deteriorated EC, for example, EC burned black. Based on the observation, they have found that if sizes of the bubbles of the $F_2/N_2$ mixture gas reacting with EC are first regulated using a gas bubble regulating column, the bubbles of the mixture gas reacting with EC are small, high reaction conversion efficiency and selectivity are assured due to a smooth reaction because the fine bubbles are uniformly dispersed in the reaction medium, and it is possible to produce highly pure FEC using only a simple purification process after the reaction is finished because a reaction solvent is not used. Thereby, the present inventors accomplished the present invention.

BRIEF DESCRIPTION OF THE SEVERAL VIEWS OF THE DRAWINGS

The above and other objects, features and advantages of the present invention will be more clearly understood from the following detailed description taken in conjunction with the accompanying drawings.

FIGS. 2a to 2d show perspective views of packing for a packing column, in which FIG. 2a illustrates a raschig ring, FIG. 2b illustrates a pall ring, FIG. 2c is a front view of a structure packing, and FIG. 2d is a plane view of the structure packing.

DETAILED DESCRIPTION OF THE INVENTION

In a method of the present invention, a batch process is employed, and EC liquid is directly fluorinated with $F_2/N_2$ mixture gas in the course of producing FEC from EC. The method of the present invention produces FEC with high selectivity and yield in a short reaction time of about 10 hours, and significantly improves the reaction efficiency of costly $F_2$ gas. Furthermore, the method of the present invention is characterized in that purification is conducted only through a vacuum distillation process instead of complicated purification processes, such as washing, extraction, drying, and crystallization processes. The present invention aims to provide a method of commercially mass-producing highly pure and useful FEC in a simple and economic manner while minimizing the loss of FEC.

Currently, the most useful method of producing FEC is to mix $F_2$ gas with inert gas ($N_2$) in a predetermined ratio to directly fluorinate EC. However, the direct fluorination reaction is problematic in that a raw material must be previously fluorinated to be used as a solvent or agitation must be conducted at a high speed using an agitator in a reactor in order to reduce a reaction rate, and in that complicated purification processes, such as washing, extraction, drying, distillation, and re-crystallization, must be implemented so as to separate and remove the solvent, which is used to reduce the reaction rate, after the reaction is finished. Other problems are that, even though an excess amount of $F_2$ gas is consumed in comparison with EC as a raw material and a long reaction time is needed, the efficiency of conversion into FEC and the yield of FEC as a final product are poor.

In the method of the present invention, EC liquid as a raw material is directly fluorinated with $F_2/N_2$ mixture gas to produce FEC, according to the following reaction equation.

EC+$F_2$/$N_2$→FEC+HF+byproducts (cis, trans, gem-DFEC)+unreacted $F_2$/$N_2$

When EC liquid comes into contact with $F_2/N_2$ mixture gas, $F_2/N_2$ mixture gas reacts with EC liquid while bubbling in EC liquid. If the bubbles are large, the reaction is rapid, causing local explosions, resulting in deterioration of EC. On the other hand, if the bubbles are very fine, the reaction is desirably carried out.

In a method of producing FEC by reacting EC with $F_2/N_2$ mixture gas as disclosed in Japanese Patent Laid-Open Publication No. 2000-309583, reactants are agitated using an agitator at 800 rpm so as to make the bubbles of the $F_2/N_2$ mixture gas fine and thus uniformly disperse the gas. Another characteristic of the present invention is to finely and uniformly form the bubbles of the $F_2/N_2$ mixture gas using a gas bubble regulating column which does not have any moving parts.

Figure 1:
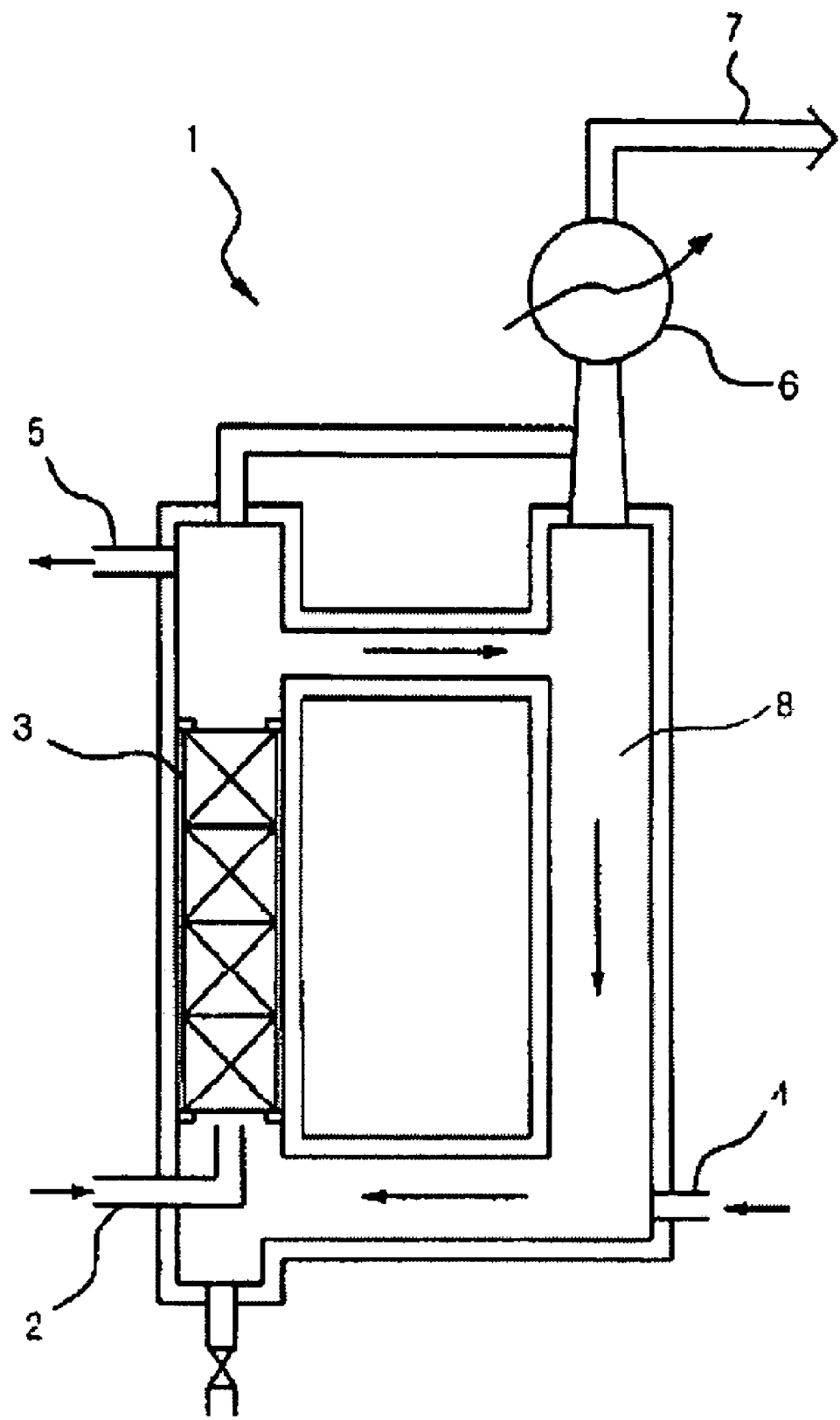
FIG. 1 is a schematic view of a device for producing 4-fluoroethylene carbonate according to the present invention.

As shown in FIG. 1, a reactor for producing FEC according to the present invention is provided with an $F_2/N_2$ mixture gas inlet at a lower part thereof, a reaction compartment having a cooling water jacket on an external surface thereof, and a vent at an upper part thereof. The reaction compartment 8 has a 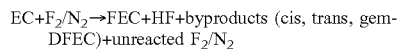

shape defined in cylinders having the "圄"shape, and a gas bubble regulating column 3 is provided in the reaction compartment 8. In detail, the reactor 1 comprises the $F_2/N_2$ mixture gas inlet 2, the gas bubble regulating column 3, a cooling water inlet 4, a cooling water outlet 5, a heat exchanger 6, an $N_2$ gas vent 7, and the reaction compartment 8. The reactor 1 also comprises units for indicating or recording a reaction temperature, an amount of contents, a flow rate, and pressure, which are used in a typical chemical reaction device, but they are not shown in FIG. 1.

$F_2/N_2$ mixture gas is fed through the $F_2/N_2$ mixture gas inlet 2 and the gas bubble regulating column 3 into the reaction compartment 8. The gas bubble regulating column 3 is used while being immersed in EC liquid. The reactor does not require additional devices, such as an agitator. A first reactor (main reactor), which has a jacket-type cooling water circulation path, and a reactor (second reactor), which has the same shape as the first reactor, are serially arranged so as to increase reaction efficiency. Each reactor is heated and cooled using external jackets.

A cylindrical reactor having an agitator is mainly used as a conventional reactor for producing FEC. Compared to the cylindrical reactor, the "圄"-shaped reactor is characterized in that it does not have moving parts, such as an agitator, the reaction compartment is long, and it has a large surface area.

Since the reaction for producing FEC is an exothermic reaction generating high reaction heat, it is necessary to supply cooling water to an external wall of the reaction compartment so as to control the reaction temperature. For a reaction compartment having a predetermined internal capacity, the surface area of the reaction compartment of the reactor according to the present invention is larger than that of a cylindrical reactor, thus it is easy to control the temperature in the present invention. In the present invention, the surface area is large and the reaction compartment is long, thus the contact time between EC and mixture gas is long, resulting in improved reaction efficiency and shortened reaction time.

In the cylindrical reactor, since it is impossible to implement the reaction while fully filling the reaction compartment with reactants, 30-40% dead volume must be assured in the reaction compartment. In the reactor of the present invention, since it is unnecessary to assure the dead volume in the reaction compartment, it is possible to reduce the size of the reaction compartment. During the reaction, the dead volume of the reactor is filled with unreacted gases, and byproducts are mostly generated by the interaction between the unreacted gases. The reactor of the present invention has a small dead volume, thus the generation of byproducts is reduced. Furthermore, since it takes a predetermined time to vent the unreacted gases, which fill the dead volume before and after the reaction, the cylindrical reactor has the disadvantage of a long production time.

Figure 2A:
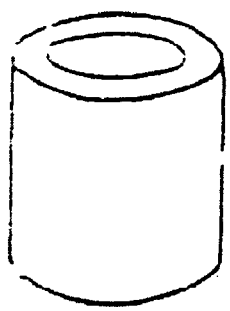
Figure 2B:
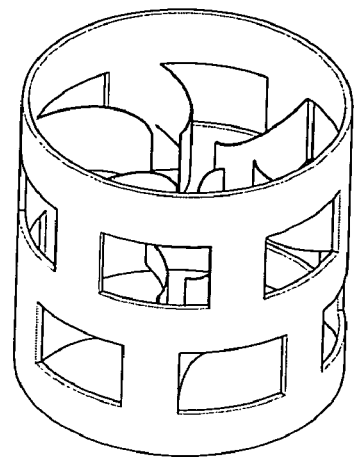
Figure 2C:
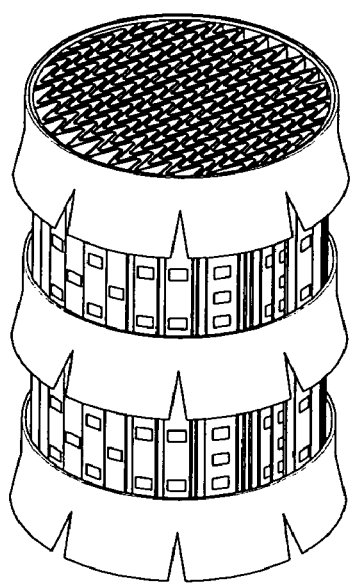
Figure 2D:
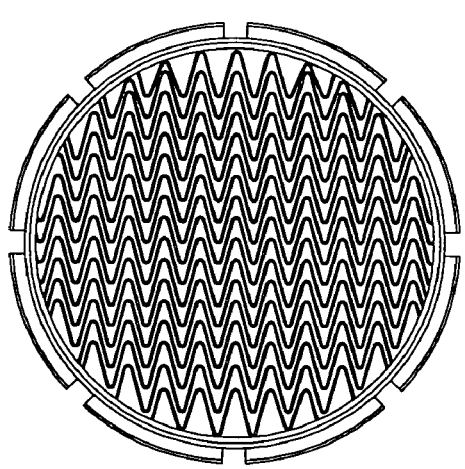

In order to efficiently mix substances in different phases, such as gas-liquid or liquid-liquid, in a chemical process, a column having a packing therein is used so as to mix the substances of the different phases while enlarging the contact area between the different phases. This column is called a packing tower or a packing column, and fillers in the column are called packings. As described above, the packing column is used in order to efficiently mix the different phases. Examples of commercially used packings include a raschig ring (FIG. 2a), a pall ring (FIG. 2b), and a structure packing (FIG. 2c) as shown in FIGS. 2a, 2b, and 2c, respectively. The pall ring is formed by providing fan-shaped branches in the raschig ring.

The ⅜" pall rings or ⅜" raschig rings made of stainless steel are packed in the gas bubble regulating column so as to efficiently mix EC liquid with $F_2$ gas. Voids caused by the nonuniformly packed packings form fine gas flow paths, and the bubbles are finely broken while mixture gas passes through these voids. The fine bubbles are uniformly dispersed in EC liquid and reacted with EC. Furthermore, a contact surface between gas and liquid is enlarged while the bubbles pass through a packed bed. This maximizes solution circulation and gas-liquid contact in the reactor, thereby assuring excellent reaction yield compared to conventional methods. $F_2/N_2$ mixture gas, which is fed into a lower part of the first reactor, stimulates the circulation of EC as the reactant, and reacts with EC in the first main reactor. The unreacted gases are recycled into a lower part of the second reactor and then reacted. The small amount of unreacted gases are vented into an absorber and then treated.

Conventionally, a mixer or an agitator, which is used to mix EC with $F_2/N_2$ mixture gas, has a moving part, such as a fan. However, in the present invention, the gas bubble regulating column, in which the packings for the packing column, such as the pall rings or the raschig rings, are packed, is provided in a reaction zone, in which EC is filled, in the reactor. Additionally, mixture gas passes through the gas bubble regulating column, thereby functioning as the mixer for mixing EC with $F_2/N_2$ mixture gas. The packings are nonuniformly packed in the gas bubble regulating column.

When $F_2/N_2$ mixture gas passes through the packed bed at a predetermined pressure, $F_2/N_2$ mixture gas comes into contact with liquid in the packed bed and is uniformly dispersed in the liquid. At this time, the flow rate of the $F_2/N_2$ mixture gas is controlled to regulate the sizes of the bubbles of the $F_2/N_2$ mixture gas formed in the EC liquid.

The sizes of the bubbles depend on the viscosity of the EC liquid, the size and structure of the packing, the height of the packed bed (or the amount of the packing), and the flow rate of $F_2/N_2$ mixture gas. The use of the packing, such as the pall ring or raschig ring, contributes to the formation of the fine bubbles of the $F_2/N_2$ mixture gas to be reacted with EC, and to sufficient gas-liquid contact between the bubbles of $F_2/N_2$ mixture gas and EC liquid, thereby improving reactivity.

In the method of the present invention, since the reaction is achieved only by directly adding $F_2/N_2$ mixture gas to EC charged in the reactor, it is unnecessary to remove a solvent during a purification process. Furthermore, the reaction device according to the present invention is characterized in that reaction stability is excellent, it is easy to control reaction heat, it is more useful in use for a short time of about 10 hours, selectivity of FEC is very high because the generation of byproducts by side reactions is insignificant, it is economically efficient because it is possible to minimize the loss of $F_2$ gas by using two serially arranged reaction devices, and it is possible to mass-produce FEC.

In the present invention, if 1.2 mol $F_2$ gas reacts and the reaction is continuously conducted in the first and second reactors, the reaction efficiency of $F_2$ gas is a very high 80-86 mol %, which is 2.2-2.5 times as high as that of the conventional method.

Furthermore, in the present invention, $F_2$ gas, which is generated from a commercially operated $F_2$ electrolytic bath, is compressed and then totally fed into the reactor without passing through a separate storage unit. 20-25 v/v % $F_2/N_2$ mixture gas is reacted at a reaction temperature of 45-60° C. and a reaction pressure of 1000-1500 mmAq, and the purification process is then conducted, thereby producing 99.8 wt % or more FEC having high purity. In this regard, as described above, the content of impurities significantly affecting performance and stability of a lithium ion secondary battery is strictly controlled so that FEC is used as an electrolyte for the battery.

According to the present invention, the purification process does not comprise a washing process using 10% $NaHCO_3$, $KHCO_3$, or ice water, an HF removing process, a dichloromethane extraction process for separating FEC, a $MgSO_4$ drying process, or a re-crystallization process, which have been employed in the prior arts. Thereby, the source of impurities due to the complicated process is removed. In the prior arts, it is difficult to reduce a content of HF to 1 wt % or less, and 50 wt % loss of FEC is inevitable because of the high solubility of FEC/EC to water.

In the present invention, the purification process is achieved sequentially using a vacuum distillation tower for removing HF from FEC, a light-heavy cut column, a product collecting tower, and an EC regeneration tower. The present invention is characterized in that EC and $F_2/N_2$ mixture gas reactants are purified only through a fractional distillation process employing vacuum distillation to produce FEC.

Since it is possible to produce highly pure FEC through the simple purification process and HF and moisture are continuously removed through several distillation towers, FEC of the present invention provides a desirable quality electrolyte, which is not obtained by rinsing using water and neutralization. The vacuum distillation is conducted so that the temperature of a reboiler is 50-150° C., the removal of HF is conducted at 60 mmHg or less, the light-heavy cut process is conducted at 40 mmHg or less, and a process of collecting FEC is implemented at 20 mmHg or less. Thereby, the present invention provides desirable electrolyte quality, such as purity, acidity, moisture content, metal ion content, and color. Furthermore, high boiling point materials (EC/undistilled FEC), which remain in each purification process, are totally recovered and then reused as raw materials, thereby minimizing the loss of EC/FEC. In the course of purifying the product gained by bringing EC into contact with $F_2/N_2$ mixture gas, if the vacuum distillation is not conducted, a high heat capacity is needed and it is necessary to use a large-scale distillation column, which is capable of providing a temperature gradient ranging from 130-250° C. because the boiling point of FEC is a high 210° C. A better understanding of the present invention may be obtained through the following examples which are set forth to illustrate, but are not to be construed as the limit of the present invention.

PREPARATION EXAMPLES

Example 1

In order to charge EC in a reactor 1, EC (m.p. 36-37° C.), which is a colorless and odorless crystal at room temperature, must be melted into a transferable solution. 10.6 kg (120.37 mol) of EC solution were charged in a reaction compartment 8 while warm water was supplied to an external cooling water jacket of the reaction compartment 8 so as to maintain the reaction compartment 8 at 45-50° C. While warm water was supplied to the cooling water jacket so as to maintain the temperature of the reactor at 45-50° C., $F_2$ gas generated from an $F_2$ electrolytic bath was fed into a mixer (not shown) and then mixed with $N_2$ gas to produce 20 v/v % $F_2/N_2$ ($F_2$ content was 20 v %) mixture gas. $F_2/N_2$ mixture gas was fed through an $F_2/N_2$ mixture gas inlet 2 at a lower part of the reactor into the reactor at a flow rate of 1960 l/h. Additionally, $F_2/N_2$ mixture gas was fed through a gas bubble regulating column 3 into the reactor. Packings were packed in the gas bubble regulating column.

In the present example, twelve hundred ⅜ raschig rings were packed in the gas bubble regulating column. The four cylindrical gas bubble regulating columns 3 were provided, and each had an internal diameter of 2", a length of 600 mm, and an internal volume of 1373 $cm^3$. When $F_2/N_2$ mixture gas passed through a raschig ring bed, which consisted of raschig rings irregularly packed in the column, the gas flowed through various flow paths and was uniformly dispersed. At this stage, if the flow rate of the mixture gas is regulated, it is possible to make the sizes of bubbles of $F_2/N_2$ mixture gas, which is formed in the EC liquid, fine using several gas bubble regulating columns. The sizes of the bubbles depend on the number of gas bubble regulating columns, the amount of packings, and the flow rate of $F_2/N_2$ mixture gas. The use of the gas bubble regulating column contributes to formation of the fine bubbles of $F_2/N_2$ mixture gas to be reacted with EC, and to uniform dispersion of the bubbles of $F_2/N_2$ mixture gas in EC liquid. The flow rate of mixture gas was controlled by a flow controller. When $F_2/N_2$ mixture gas was fed into the reactor and a reaction started to be conducted, the reaction was intensely conducted and high reaction heat was generated.

Accordingly, cooling water was supplied to the cooling water jacket and a reaction temperature was maintained at 55±3° C. The arrows in the reactor shown in FIG. 1 denote the flow direction of EC. Brine at −15° C. was fed into a heat exchanger at an upper part of the reactor so as to maintain a temperature of a lower part of the heat exchanger at 27±2° C. A solenoid valve was provided at a pipe for discharging unreacted gases therethrough into an absorber and a device for controlling fine pressure was connected thereto so as to control the pressure in the reactor. The pressure was controlled to 1000+30 mmAq. When the flow rate of $F_2$ gas was 1.2 mol based on EC charged in the reactor at an initial stage, the reaction was finished. After the end of the reaction, remaining gas was removed from the reactor using 500 L/hr $N_2$ for 30 min.

The reaction results were that the total amount of product was 13.14 kg, HF was 11.63 wt % (1.05 kg), FEC was 75.37 wt % (8.75 kg, 82.5 mol), and DFEC was 3.0 wt % (0.35 kg, 2.85 mol). A mole number of reacted $F_2$ was 88.2 mol, conversion efficiency of $F_2$ was 61.1%, and selectivity of FEC was 93.5%. Yield of FEC was 57.1% based on $F_2$.

Example 2

The reaction was conducted under the same conditions as example 1 with the exception of the following conditions. Two reactors having the same shape were employed while being serially connected. 10.6 kg of EC solution were charged in a first reactor as a main reactor and in a second reactor, and 20 v/v % $F_2/N_2$ mixture gas as reactant gas was fed into the first reactor to conduct a first reaction. Unreacted gases, which were generated in the first reaction, were fed into the second reactor so as to be reused. The other reaction conditions were the same as example 1.

As a result, the total amount of product was 25.3 kg, HF was 9.96 wt % (2.52 kg), FEC was 52.74 wt % (12.01 kg, 113.2 mol), and DFEC was 2.06 wt % (0.47 kg, 3.73 mol). A mol number of reacted $F_2$ was 116.9 mol, which meant that conversion efficiency of $F_2$ was 80.93%, and selectivity of FEC was 96.8%. Yield of FEC was 78.4% based on $F_2$.

Example 3

The reaction was conducted under the same conditions as example 2 with the exception of the following conditions. 10.6 kg of EC solution were charged in a first reactor as a main reactor, and 10.6 kg of EC/FEC solution, which contains 35 wt % (34.8 mol) FEC, were charged in a second reactor. 20 v/v % $F_2/N_2$ mixture gas as reactant gas was fed into the first reactor to conduct a first reaction. Unreacted gases, which were generated in the first reaction, were fed into the second reactor so as to be reused. The other reaction conditions were the same as example 2.

As a result, the total amount of product was 25.01 kg, HF was 11.79 wt % (2.95 kg), FEC was 73.65 wt % (16.24 kg, 153.1 mol), and DFEC was 2.99 wt % (0.66 kg, 5.32 mol). A mol number of reacted $F_2$ was 124.8 mol, which meant that conversion efficiency of $F_2$ was 86.4%, and selectivity of FEC was 94.8%. Yield of FEC was 81.9% based on $F_2$.

Example 1 employed one reactor 1, but examples 2 and 3 employed two reactors 1 which were serially connected to each other. When two reactors were used, unreacted $F_2$ gas, discharged from the first reactor, was recovered, provided to form $F_2/N_2$ mixture gas, and fed into the second reactor in the same manner as the first reactor.

Compared to the use of one reactor, the use of two reactors is more effective to reduce the loss of $F_2$ gas and to increase the amount of FEC produced.

PURIFICATION EXAMPLE

Example 4

Examples 1, 2, and 3 were conducted in a batch manner, and the products therefrom were stored in a storage tank while being mixed.

After the reaction was finished, the products were transferred to an HF removal column and subjected to a vacuum distillation process therein. A wire gauze type packing, alias a structure packing, as shown in FIG. 2c was packed in a distillation column to improve distillation efficiency. Removed at a top part of the distillation column, HF was caught by a liquid nitrogen trap installed before a vacuum pump. Distillation efficiency was increased according to an increase in vacuum pressure at the same reboiler temperature, and was increased according to an increase in temperature at the same pressure. In the present example, a distillation temperature was 95±1° C. and pressure was 35±3 mmHg. In this respect, it is possible to implement distillation at the distillation temperature of 60-120° C. and distillation pressure of 30-140 mmHg.

As a result, 19.8 kg of product, which contained 71.8 wt % FEC, 12.3 wt % HF, 2.8 wt % DFEC, and 13.1 wt % EC, were distilled to collect 16.23 kg of FEC-containing organic mixture (95.5 wt % based on FEC), which contained 83.7 wt % FEC, 0.1 wt % HF (removal efficiency 99.2 wt %), 0.49 wt % DFEC, and 15.71 wt % EC, in a separate storage tank. The above procedure was repeated to produce the HF-free mixture, which contained 82-84 wt % FEC, 0.1-0.13 wt % HF, 0.4-0.6 wt % DFEC, and 15-17 wt % EC.

The product, from which HF was removed in the HF removal column, was fed from the storage tank to a light-heavy cut column. DFEC and the small amount of HF were removed at a top part of the light-heavy cut column, and coarse FEC containing 92-95% FEC was collected at a middle part of the column. In the present example, the light-heavy cut column was operated at a distillation temperature of 120±1° C. and a pressure of 25±2 mmHg. In this respect, it is possible to operate the column at a distillation temperature of 90-180° C. and a distillation pressure of 20-100 mmHg.

As a result, 20.1 kg of FEC-containing organics, which contained 82.6 wt % FEC, 0.12 wt % HF, 0.46 wt % DFEC, and 16.82 wt % EC, were distilled to collect 15.87 kg of coarse FEC (89.1 wt % based on FEC), which contained 93.22 wt % FEC, 0.009 wt % HF, and 0.21 wt % DFEC, in a separate storage tank. The above procedure was repeated to produce a distillate, which contained 92-94 wt % FEC, 0.007-0.012 wt % HF, and 0.15-0.3 wt % DFEC. Additionally, high boiling point materials remaining in a reboiler were recycled into the reactor or an EC regeneration column to be reused.

Coarse FEC, which was purified in the light-heavy cut column, was transferred to a final product collection column, DFEC and the small amount of unremoved HF were removed at a top part of the column, and a FEC final product was collected at a middle part of the column. In the present example, the column was operated at a distillation temperature of 94-96° C. and pressure of 4 mmHg or less. In this respect, it is possible to operate the column at the distillation temperature of 60-130° C. and distillation pressure of 1-100 mmHg.

As a result, 20.0 kg of coarse FEC, which contained 93.84 wt % FEC, 0.008 wt % HF, 0.19 wt % DFEC, and 5.96 wt % EC, were distilled to collect 16.53 kg of FEC product (88.0 wt % based on FEC), which contained 99.89 wt % FEC, 0.003 wt % HF, and 0.10 wt % DFEC, in a storage tank. Additionally, coarse FEC remaining in a reboiler was recycled into the light-heavy cut column to be reused.

Example 4 was implemented through a few stages, thus the composition of the product of the preceding stage is different from that of the starting material of the next stage.

As described above, the present invention provides a method of producing FEC, in which EC directly reacts with $F_2/N_2$ mixture gas. The method is advantageous in that a purification process is simple, and it is possible to produce FEC at high conversion efficiency and selectivity.

We claim:

1. A method of producing 4-fluoroethylene carbonate, said method comprising:

feeding a mixture gas of fluorine gas and nitrogen gas into a reactor having ethylene carbonate charged therein, so as to react the ethylene carbonate with the mixture gas of the fluorine gas and the nitrogen gas, wherein the mixture gas is regulated to have a desired bubble size while passing through a gas bubble regulating column, in which a packing for a packed column is packed.

2. The method as set forth in claim 1, wherein the packing for the packed column comprises a raschig ring, a pall ring, or a structure packing.

3. A method of purifying 4-fluoroethylene carbonate, said method comprising:

distilling 4-fluoroethylene carbonate, containing hydrofluoric acid (HF) produced by reacting ethylene carbonate with fluorine and nitrogen gases, unreacted ethylene carbonate, and difluoroethylene carbonate (DFEC), in a vacuum so as to separate and purify hydrofluoric acid, ethylene carbonate, and difluoroethylene carbonate, thereby producing highly pure 4-fluoroethylene carbonate.

4. The method as set forth in claim 3, said method further comprising:

conducting fractional distillation of 4-fluoroethylene carbonate, which contains hydrofluoric acid, ethylene carbonate, and difluoroethylene carbonate, in a fractional distillation column at a temperature of 60-120° C. and a pressure of 30-140 mmHg so as to separate and remove hydrofluoric acid;

conducting re-distillation at a temperature of 90-160° C. and a pressure of 20-100 mmHg to separate and remove ethylene carbonate, difluoroethylene carbonate, and remaining hydrofluoric acid; and conducting re-distillation at a temperature of 60-130° C. and a pressure of 1-100 mmHg to produce highly pure 4-fluoroethylene carbonate.

5. A reactor for producing 4-fluoroethylene carbonate, said reactor comprising:

an $F_2/N_2$ mixture gas inlet;

a reaction compartment having a cooling water jacket provided on an external surface thereof, and comprised of cylinders to have a 'H' shape;

a vent provided at an upper part thereof, and a gas bubble regulating column, in which a packing for a packed column is packed and which is provided in the reaction compartment.

* * * * *